US009981937B2

(12) United States Patent
Kropf et al.

(10) Patent No.: US 9,981,937 B2
(45) Date of Patent: May 29, 2018

(54) ORTHOFORMIC ACID ESTERS AS PRO-FRAGRANCES

(71) Applicant: Henkel AG & Co. KGaA, Duesseldorf (DE)

(72) Inventors: Christian Kropf, Hilden (DE); Thomas Gerke, Duesseldorf (DE); Ursula Huchel, Cologne (DE); Thomas J. J. Mueller, Duesseldorf (DE); Julian Papadopoulos, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days. days.

(21) Appl. No.: 15/539,338

(22) PCT Filed: Dec. 8, 2015

(86) PCT No.: PCT/EP2015/078986
§ 371 (c)(1),
(2) Date: Jun. 23, 2017

(87) PCT Pub. No.: WO2016/096540
PCT Pub. Date: Jun. 23, 2016

(65) Prior Publication Data
US 2017/0349565 A1 Dec. 7, 2017

(30) Foreign Application Priority Data

Dec. 17, 2014 (DE) .................. 10 2014 226 194

(51) Int. Cl.
| | | |
|---|---|---|
| *A61K 8/18* | (2006.01) | |
| *A61K 8/00* | (2006.01) | |
| *C07D 317/34* | (2006.01) | |
| *C11B 9/00* | (2006.01) | |
| *C07C 69/003* | (2006.01) | |
| *C07C 69/74* | (2006.01) | |

(52) U.S. Cl.
CPC .......... *C07D 317/34* (2013.01); *C07C 69/003* (2013.01); *C07C 69/74* (2013.01); *C11B 9/0076* (2013.01)

(58) Field of Classification Search
USPC ............................................ 512/12, 11, 8, 1
See application file for complete search history.

(56) References Cited

U.S. PATENT DOCUMENTS

| | | |
|---|---|---|
| 4,406,686 A | 9/1983 | Walker |
| 6,022,921 A | 2/2000 | Achenbach et al. |

FOREIGN PATENT DOCUMENTS

| | | | |
|---|---|---|---|
| CN | 103588749 | * | 2/2014 |
| CN | 103588749 A | | 2/2014 |
| CN | 103804684 A | | 5/2014 |
| EP | 0067361 A2 | * 12/1982 | ........... C07D 317/34 |
| EP | 0067361 A2 | | 12/1982 |
| WO | 9943667 A1 | | 9/1999 |

OTHER PUBLICATIONS

Halbritter et al, EP 0067361 Machine Translation, Dec. 22, 1982 (Year: 1982).*
Xu et al, CN 103588749 Machine Translation, Feb. 19, 2014 (Year: 2014).*
Paez Beracierta, A. et al., "Synthesis of the (+/−)-Dimethylethers of Agatharesinol, Sequirin-A, and Hinokiresinol, Related Norlignans of Coniferae", Tetrahedron Letters No. 27, 1976, pp. 2367-2370, Pergamon Press, Great Britain.
Khatuntsev, I. I. et al., "Homolytic Additiono of 2-Ethoxy-1,3-Dioxolane to 1-Decene", Izvestiya Akademii Nauk SSSR, Seriy Khimicheskaya, vol. 9, 1985, pp. 2051-2053.
Rasulov, S. A. et al., "Synthesis and Properties 2-Ethoxy-4-(Dialkylaminomethyl)-1,3-Dioxolanes".
EPO, International Search Report and Written Opinion issued in International Patent Application No. PCT/EP2015/078986, dated Feb. 23, 2016.

* cited by examiner

*Primary Examiner* — Jessica Whiteley
(74) *Attorney, Agent, or Firm* — Lorenz & Kopf LLP

(57) ABSTRACT

The disclosure relates to special orthoformic acid esters of formula (I), as defined herein, which can be used as thermally labile and acid-labile fragrance storage substances. The disclosure further relates to detergents and cleaning agents, cosmetic agents and air freshening products containing such orthoformic acid esters, as well as to a method for lastingly fragrancing surfaces.

18 Claims, No Drawings

ORTHOFORMIC ACID ESTERS AS PRO-FRAGRANCES

CROSS-REFERENCE TO RELATED APPLICATION

This application is a U.S. National-Stage entry under 35 U.S.C. § 371 based on International Application No. PCT/EP2015/078986, filed Dec. 8, 2015, which was published under PCT Article 21(2) and which claims priority to German Application No. 10 2014 226 194.5, filed Dec. 17, 2014, which are all hereby incorporated in their entirety by reference.

TECHNICAL FIELD

The present disclosure lies in the field of fragrance storage substances, such as those used for example in the field of detergents or cleaning agents, cosmetic agents and air freshening products. The disclosure relates to special orthoformic acid esters which act as thermally labile and acid-labile fragrance storage substances. The present disclosure further relates to detergents and cleaning agents, cosmetic agents and air freshening products containing such orthoformic acid esters. It further relates to a method for lastingly fragrancing surfaces and also to a method for lastingly fragrancing rooms.

BACKGROUND

Detergents and cleaning agents and cosmetic agents usually contain fragrances which give the agents a pleasant odor. In this case, the odor of other ingredients is masked by the fragrances, so that the consumer is given a pleasant odor impression.

Particularly in the field of detergents, fragrances are among the important constituents of the detergent composition since both the wet and the dry laundry should have a pleasant and fresh smell. In general, fragrances are readily volatile substances and therefore a long-lasting fragrance effect is difficult to achieve. Particularly in the case of fragrances which represent the fresh and light notes of the perfume, and which evaporate particularly quickly due to their relatively high vapor pressure, the desired longevity of the fragrance impression is difficult to achieve. Fragrance storage substance molecules are known in the prior art and provide a possibility of releasing fragrances in a delayed manner. Depending on the respective fragrance storage molecule, the breaking of a covalent bond in the fragrance storage substance molecule is induced by the effect of electromagnetic radiation, heat, or by reaction with chemical substances, such as acid, and a fragrance is released. However, the fragrance intensity in the case of conventional fragrance storage molecules is low and the fragrance effect is only short-lived. Furthermore, with these storage molecules, it is not possible to achieve both an immediate release and a delayed release of the fragrances. There is therefore a need for fragrance storage molecules which can release fragrances both immediately and also in a delayed manner over a longer period of time.

BRIEF SUMMARY

A compound of formula (I) is provided herein:

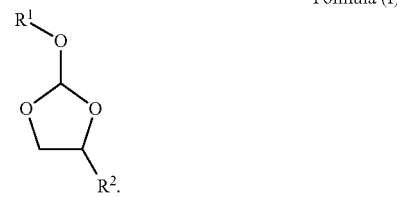

Formula (I)

$R^1$ and $R^2$ are each independently of one another selected from the group of: a linear, aliphatic, olefinic or open-chain organic residue having 2 to 20 carbon atoms and 0 to 10 heteroatoms selected from N, O, S and Si; a branched or cyclic organic residue having 3 to 20 carbon atoms and 0 to 10 heteroatoms selected from N, O, S and Si; and an aromatic or heteroaromatic organic residue having 4 to 20 carbon atoms and 0 to 10 heteroatoms selected from N, O, S and Si.

DETAILED DESCRIPTION

The following detailed description is merely exemplary in nature and is not intended to limit the disclosure or the application and uses of the subject matter as described herein. Furthermore, there is no intention to be bound by any theory presented in the preceding background or the following detailed description.

It has now surprisingly been found that certain orthoformic acid esters release the stored fragrances both immediately and also in a delayed manner. This property is based on the fact that these orthoformic acid esters are both thermally labile and acid-labile. An immediate release of the stored fragrances is thus brought about under the effect of heat, and a delayed release is brought about under the effect of acid.

An immediate release, that is to say a prompt release, is advantageous for example when the compound as contemplated herein is applied to a textile and the latter is then heated, for example during washing operations at elevated temperature, during drying using a tumble dryer, or during ironing, since the consumer is given a pleasant fragrance impression. Furthermore, it is also possible to use the compound as contemplated herein and the heat-induced immediate release of the stored fragrance when cooking, frying or baking.

The delayed release of the fragrance takes place under the effect of Lewis and/or Brønsted acids. This takes place for example when the compound as contemplated herein is applied to a textile and the latter comes into contact with the skin. Since the skin has a slightly acidic pH, the release is brought about as a result of this contact. The compound as contemplated herein thus releases fragrances over a long period of time and thus ensures a long-lasting fragrance effect, particularly in connection with textile treatment.

For example, when using the compound as contemplated herein in a laundry treatment agent, such as for example a detergent and softener, it was possible to observe an improved long-term fragrance effect of the treated laundry. The agents as contemplated herein moreover make it possible to reduce the total amount of fragrance contained in the agent yet still achieve odor advantages on the washed textiles, particularly with regard to the sensation of freshness.

In a first aspect, therefore, the disclosure relates to compounds of formula (I)

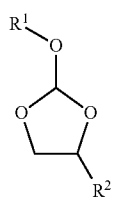

Formula (I)

wherein
$R^1$ and $R^2$ are each independently of one another selected from
a linear, aliphatic, olefinic or open-chain organic residue having 2 to 20 carbon atoms, in particular 2 to 12 carbon atoms, and 0 to 10 heteroatoms selected from N, O, S and Si;
a branched or cyclic organic residue having 3 to 20 carbon atoms, in particular 3 to 12 carbon atoms, and 0 to 10 heteroatoms selected from N, O, S and Si; and
an aromatic or heteroaromatic organic residue having 4 to 20 carbon atoms, in particular 4 to 12 carbon atoms, and 0 to 10 heteroatoms selected from N, O, S and Si.

In a further aspect, the present disclosure relates to a detergent or cleaning agent containing at least one compound of formula (I) as described herein.

A further subject matter as contemplated herein is a cosmetic agent which comprises at least one of the compound of formula (I) described herein.

Yet another subject matter as contemplated herein is an air freshening product which contains at least one of the compound of formula (I) as contemplated herein.

Finally, the present disclosure is also directed to a method for lastingly fragrancing surfaces.

As used herein, "at least one" refers to one or more, for example 2, 3, 4, 5, 6, 7, 8, 9 or more. In connection with constituents of the compound described herein, this indication does not refer to the absolute amount of molecules but rather to the type of constituent. Therefore, "at least one compound of formula (I)" means for example one or more different compounds of formula (I), that is to say one or more different types of compounds. Together with specified amounts, the amount indications refer to the total amount of the correspondingly designated type of constituent, as already defined above.

In various embodiments, $R^1$ contains 1, 2, 3 or 4 heteroatoms selected from O, S, N and Si, in particular with the proviso that the residue $R^1$ contains for each heteroatom at least one carbon atom.

In various other embodiments, the residue $R^2$ also contains 1, 2, 3 or 4 heteroatoms selected from O, S, N and Si, in particular with the proviso that the residue $R^2$ contains for each heteroatom at least one carbon atom.

In various embodiments as contemplated herein, $R^1$ and $R^2$ are independently selected from the group of substituted or unsubstituted, linear or branched alkyl, alkenyl or alkynyl having up to 20, preferably up to 12 carbon atoms, substituted or unsubstituted, linear or branched heteroalkyl, heteroalkenyl or heteroalkynyl having up to 20, preferably up to 12 carbon atoms, and 1 to 6, preferably 1 to 4 heteroatoms selected from O, S and N, substituted or unsubstituted aryl having up to 20, preferably up to 12 carbon atoms, substituted or unsubstituted heteroaryl having up to 20, preferably up to 12 carbon atoms, and 1 to 6, preferably 1 to 4 heteroatoms selected from O, S and N, cycloalkyl or cycloalkenyl having up to 20, preferably up to 12 carbon atoms, and heterocycloalkyl or heterocycloalkenyl having up to 20, preferably up to 12 carbon atoms, and 1 to 6, preferably 1 to 4 heteroatoms selected from O, S and N.

"Alkyl" refers to a saturated aliphatic hydrocarbon including straight-chain and branched-chain groups. Preferably, the alkyl group has 1 to 10 carbon atoms (when a numerical range, for example "1 to 10," is indicated herein, this means that said group, in this case the alkyl group, may have 1 carbon atom, 2 carbon atoms, 3 carbon atoms, etc., up to and including 10 carbon atoms). In particular, the alkyl may be a medium alkyl which has 1 to 6 carbon atoms, or a lower alkyl which has 1 to 4 carbon atoms, for example methyl, ethyl, n-propyl, isopropyl, butyl, isobutyl, tert-butyl, etc.

"Alkenyl" refers to an alkyl group, as defined herein, which consists of at least two carbon atoms and at least one carbon-carbon double bond, for example ethenyl, propenyl, butenyl or pentenyl, and structural isomers thereof such as 1- or 2-propenyl, 1-, 2- or 3-butenyl, etc.

"Alkynyl" refers to an alkyl group, as defined herein, which consists of at least two carbon atoms and at least one carbon-carbon triple bond, for example ethynyl (acetylene), propynyl, butynyl or pentynyl, and structural isomers thereof as described above.

"Heteroalkyl," "heteroalkenyl" and "heteroalkynyl," as used herein, refer to alkyl, alkenyl or alkynyl groups, as defined above, in which 1 or more carbon atoms are replaced by heteroatoms, in particular selected from O, S, N and Si, for example ethoxyethyl, ethoxyethenyl, isopentoxypropyl, etc.

A "cycloalkyl" group refers to monocyclic or polycyclic (multiple rings which have common carbon atoms) groups, in particular of 3 to 8 carbon atoms, in which the ring has no complete conjugated pi electron system, for example cyclopropyl, cyclobutyl, cyclopentyl, cyclohexyl, cyclobutenyl, cyclopentenyl, cyclohexenyl, etc. Examples of cycloalkyl groups are cyclopropane, cyclobutane, cyclopentane, cyclopentene, cyclohexane, adamantane, cyclohexadiene, cycloheptane and cycloheptatriene.

"Aryl" refers to monocyclic or polycyclic (that is to say rings which have adjacent carbon atom pairs in common) groups of in particular 6 to 14 carbon ring atoms which have a complete conjugated pi electron system. Examples of aryl groups are phenyl, naphthalenyl and anthracenyl.

A "heteroaryl" group refers to a monocyclic or polycyclic (that is to say rings which share an adjacent ring atom pair) aromatic ring of in particular 5 to 10 ring atoms, wherein one, two, three or four ring atoms are nitrogen, oxygen or sulfur, and the remainder is carbon. Examples of heteroaryl groups are pyridyl, pyrrolyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadiazolyl, 1,2,5-oxadiazolyl, 1,3,4-oxadiazolyl, 1,3,4-triazinyl, 1,2,3-triazinyl, benzofuryl, isobenzofuryl, benzothienyl, benzotriazolyl, isobenzothienyl, indolyl, isoindolyl, 3H-indolyl, benzimidazolyl, benzothiazolyl, benzoxazolyl, quinolizinyl, quinazolinyl, phthalazinyl, quinoxalinyl, cinnolinyl, naphthyridinyl, quinolyl, isoquinolyl, tetrazolyl, 5,6,7,8-tetrahydroquinolyl, 5,6,7,8-tetrahydroisoquinolyl, purinyl, pteridinyl, pyridinyl, pyrimidinyl, carbazolyl, xanthenyl or benzoquinolyl.

A "heterocycloalkyl" group refers to a monocyclic or fused ring of 5 to 10 ring atoms, which contains one, two or three heteroatoms selected from N, O and S, the remainder of the ring atoms being carbon. A "heterocycloalkenyl"

group additionally contains one or more double bonds. However, the ring has no complete conjugated pi electron system. Examples of heteroalicyclic groups are pyrrolidine, piperidine, piperazine, morpholine, imidazolidine, tetrahydropyridazine, tetrahydrofuran, thiomorpholine, tetrahydropyridine, and the like.

"Substituted," as used herein in connection with the substituents and residues as contemplated herein means that in the group in question one or more H atoms are replaced by other functional groups, the latter being selected in particular from those containing one or more heteroatoms. In various embodiments, the substituents are selected from =O, =S, —OH, —SH, —NH$_2$, —NO$_2$, —CN, —F, —Cl, —Br, C$_{1-10}$ alkyl, C$_{2-10}$ alkenyl, C$_{2-10}$ alkynyl, C$_{3-8}$ cycloalkyl, C$_{6-14}$ aryl, a 5- to 10-membered heteroaryl ring in which 1 to 4 ring atoms independently are nitrogen, oxygen or sulfur, and a 5- to 10-membered heteroalicyclic ring in which 1 to 3 ring atoms independently are nitrogen, oxygen or sulfur.

In various embodiments, R$^1$ contains at least one carbonyl group (—C(=O)—), an aromatic or heteroaromatic group, wherein the latter may be substituted, in particular in the alpha or beta position, to form the oxygen atom of the orthoester function. In various embodiments, therefore, R$^1$ is a residue of formula —C(O)—R$^3$, —CH$_2$—C(O)—R$^3$, -aryl, -heteroaryl, CH$_2$-aryl or CH$_2$-heteroaryl, wherein R$^3$ is selected from the group of hydrogen, substituted or unsubstituted, linear or branched alkyl, alkenyl or alkynyl having up to 20, preferably up to 10 carbon atoms, substituted or unsubstituted, linear or branched heteroalkyl, heteroalkenyl or heteroalkynyl having up to 20, preferably up to 10 carbon atoms, and 1 to 6, preferably 1 to 4 heteroatoms selected from O, S and N, substituted or unsubstituted aryl having up to 20, preferably 6 to 10 carbon atoms, substituted or unsubstituted heteroaryl having up to 20, preferably 4 to 10 carbon atoms, and 1 to 6, preferably 1 to 4 heteroatoms selected from O, S and N, cycloalkyl or cycloalkenyl having up to 20, preferably 5 to 10 carbon atoms, and heterocycloalkyl or heterocycloalkenyl having up to 20, preferably 4 to 10 carbon atoms, and 1 to 6, preferably 1 to 4 heteroatoms selected from O, S and N.

In various embodiments, R$^1$ is a substituted or unsubstituted, linear or branched alkyl having 1 to 5, particularly preferably 1 to 3 carbon atoms, and most preferably methyl or ethyl. In various other embodiments, R$^1$ is a residue of formula —C(O)—R$^3$ and R$^3$ is a substituted or unsubstituted, linear or branched alkyl having up to 5 and preferably up to 3 carbon atoms, particularly preferably methyl.

In various embodiments, R$^1$ has a molecular weight of up to 300 g/mol, in particular ≤250 g/mol.

In various embodiments of the compound of formula (I), R$^2$ is an organic residue having 4 to 10 carbon atoms and/or contains at least one, preferably at least 2, more preferably at least 3 heteroatoms selected from N, O, S, Si, F, Cl and Br, and/or contains at least one cyclic group and/or contains at least one carbonyl group (—C(=O)—. In preferred embodiments, R$^2$ is an organic residue having 4 to 10 carbon atoms and contains at least one carbonyl group (—C(=O)— and optionally at least one further heteroatom selected from N, O and S, in particular O. With particular preference, R$^2$ is a residue of formula C$_{1-10}$-alkyl-O—(CH$_2$)$_p$—C(O)O—(CH$_2$)$_q$—, wherein p and q independently are 0 or an integer from 1 to 6. In various embodiments, R$^2$ also has a molecular weight of up to 300 g/mol, in particular ≤250 g/mol.

The residue R$^2$ of formula (I) is in particular a residue derived from a fragrance alkene, and the residue R$^1$ may be in particular a residue derived from a fragrance alcohol.

"Derived residue," as used in this context, refers for example to the residue R$^2$ which is obtained when the unsaturated group of a fragrance alkene is added to orthoformic acid or to an orthoformic acid ester and the two carbon atoms of the double bond form ring atoms 4 and 5 of the 1,3-dioxolane ring of formula (I). For the case where the fragrance alkene is allyl isoamyl glycolate ((CH$_3$)$_2$CH—CH$_2$—CH$_2$—O—CH$_2$—C(O)O—CH$_2$—CH=CH$_2$), the residue R$^2$ would thus be ((CH$_3$)$_2$CH—CH$_2$—CH$_2$—O—CH$_2$—C(O)O—CH$_2$—.

Under the effect of a Brønsted and/or Lewis acid, the compound of formula (I) breaks down into the alcohol R$^1$—OH, which may be a fragrance alcohol, and the carboxylic acid R$^3$—COOH, CO$_2$ and the fragrance alkene. As contemplated herein, all fragrance alkenes or fragrance alcohols known in the prior art and suitable for this purpose can be used.

A "Brønsted acid," as used herein, is a compound which gives off one or more protons (H$^+$) and transfers said proton(s) to a reaction partner, the so-called "Brønsted base." As contemplated herein, use can be made of any conventional Brønsted acid which is suitable for the purpose as contemplated herein. These include for example both weak and strong acids, such as formic acid, acetic acid, phosphoric acid or mixtures thereof.

A "Lewis acid," as used herein, is an electrophilic electron pair acceptor. As contemplated herein, use can be made of any conventional Lewis acid which is suitable for the purpose as contemplated herein. These include for example some metal cations but also, in general, compounds with an incomplete or unstable electron octet.

In various embodiments, the fragrance alkene or the fragrance alcohol which is obtained through cleavage of the compound of formula (I) is selected from the group of acetovanillone, allyl amyl glycolate, allyl isoamyl glycolate, alpha-amyl cinnamyl alcohol, anisyl alcohol, benzoin, benzyl alcohol, benzyl salicylate, 1-butanol, butyl lactate, 2-t-butyl-5-methylphenol, 2-t-butyl-6-methylphenol, carvacrol, carveol, 4-carvomenthenol, cedrol, cetyl alcohol, cinnamic alcohol, citronellol, o-cresol, m-cresol, p-cresol, crotyl alcohol, decahydro-2-naphthol, 1-decanol, 1-decen-3-ol, 9-decen-1-ol, diethyl malate, diethyl tartrate, dihydrocarveol, dihydromyrcenol, 2,6-diisopropylphenol, dimethicone copolyol, 2,6-dimethoxyphenol, 1,1-dimethoxy-3,7-dimethyloctan-7-ol, 2,6-dimethyl-4-heptanol, 2,6-dimethylheptan-2-ol, 6,8-dimethyl-2-nonanol, 3,7-dimethyl-2,6-octadien-1-ol, 3,7-dimethyl-1,6-octadien-3-ol, 3,7-dimethyl-1-octanol, 3,7-dimethyl-3-octanol, 3,7-dimethyl-6-octen-1-ol, 3,7-dimethyl-7-octen-1-ol, dimetol, 2-ethylfenchol, 4-ethylguaiacol, 2-ethyl-1-hexanol, ethyl 2-hydroxybenzoate, ethyl 3-hydroxybutyrate, 3-ethyl-2-hydroxy-2-cyclopenten-1-one, ethyl 2-hydroxycaproate, ethyl 3-hydroxyhexanoate, ethyl lactate, ethyl maltol, p-ethylphenol, ethyl salicylate, eugenol, farnesol, fenchyl alcohol, geraniol, glucose pentaacetate, glycerol, glyceryl monostearate, guaiacol, 1-heptanol, 2-heptanol, 3-heptanol, cis-4-heptenol, cis-3-heptenol, n-hexanol, 2-hexanol, 3-hexanol, cis-2-hexenol, cis-3-hexenol, trans-3-hexenol, 4-hexenol, cis-3-hexenyl hydrocinnamyl alcohol, 2-hydroxybenzoate, 2-hydroxyacetophenone, 4-hydroxybenzyl alcohol, 3-hydroxy-2-butanone, hydroxycitronellal, 4-(4-hydroxy-3-methoxyphenyl)-2-butanone, 2-hydroxy-3-methyl-2-cyclopenten-1-one, 4-(p-hydroxyphenyl)-2-butanone, 2-hydroxy-3,5,5-trimethyl-2-cyclohexenone, delta-isoascorbic acid, isoborneol, isoeugenol, isophytol, isopropyl alcohol, p-isopropyl benzyl alcohol, 4-isopropylcyclohexanol, 3-isopropylphenol, 4-isopropylphenol, 2-isopropylphenol, isopulegol, lauryl alcohol, linalool, maltol, menthol, 4-methoxybenzyl alcohol, 2-methoxy-4-methylphenol, 2-methoxy-4-propylphenol, 2-methoxy-4-vinylphenol, α-methylbenzyl alcohol, 2-methylbutanol, 3-methyl-2-butanol, 3-methyl-2-buten-1-ol, 2-methyl-3-buten-2-ol, methyl 2,4-dihydroxy-3,6-dimethylbenzoate, 4-methyl-2,6-dimethoxyphenol, methyl N-3,7-dimethyl-7-hydroxyoctylideneanthranilate, methyl 3-hydroxyhexanoate, 6-methyl-5-hepten-2-ol, 2-methylpentanol, 3-methyl-3-pentanol, 2-methyl-4-phenylbutan-2-ol, 2-methyl-3-phenylpropan-2-ol, methyl salicylate, 3-methyl-5-(2,2,3-trimethyl-3-cyclopenten-1-yl)-4-penten-2-ol, 2-methyl-2-vinyl-5-(1-hydroxy-1-methylethyl)-3,4-dihydrofuran, myrtenol, neohesperidin dihydrochalcone, neomenthol, nerol, nerolidol, trans-2-cis-6-nonadienol, 1,3-nonanediol acetate, nonadyl, 2-nonanol, cis-6-nonen-1-ol, trans-2-nonen-1-ol, nonyl alcohol, 1-octanol, 2-octanol, 3-octanol, cis-3-octen-1-ol, cis-2-octen-1-ol, trans-2-octen-1-ol, cis-6-octen-1-ol, cis-octen-1-ol, 1-octen-3-ol, oleyl alcohol, patchouli alcohol, 3-pentanol, n-pentanol, 2-pentanol, 1-penten-1-ol, cis-2-penten-1-ol, perillyl alcohol, 2-phenoxyethanol arabinogalactan, beta-phenethyl alcohol, phenethyl salicylate, phenol, phenylacetaldehyde glyceryl acetal, 3-phenyl-1-pentanol, 5-phenyl-1-pentanol, 1-phenyl-1-pentanol, 1-phenyl-2-pentanol, 1-phenyl-3-methyl-1-pentanol, phytol, pinacol, polyalkylene glycol, Polysorbate 20, Polysorbate 60, Polysorbate 80, prenol, n-propanol, propenyl guaethol, propylene glycol, 2-propylphenol, 4-propylphenol, resorcinol, retinol, salicylaldehyde, sorbitan monostearate, sorbitol, stearyl alcohol, syringaldehyde, alpha-terpineol, tetrahydrogeraniol, tetrahydrolinalool, tetrahydromyrcenol, thymol, triethyl citrate, 1,2,6-trihydroxyhexane, p-α,α-trimethylbenzyl alcohol, 2-(5,5,6-trimethylbicyclo[2.2.1]hept-2-yl)cyclohexanol, 5-(2,2,3-trimethyl-3-cyclopentenyl)-3-methylpentan-2-ol, 3,7,11-trimethyl-2,6,10-dodecatrien-1-ol, 3,7,11-trimethyl-1,6,10-dodecatrien-3-ol, 3,5,5-trimethyl-1-hexanol, 10-undecen-1-ol, undecyl alcohol, vanillin, o-vanillin, vanillyl butyl ether, 4-vinylphenol, 2,5-xylenol, 2,6-xylenol, 3,5-xylenol, 2,4-xylenol, xylose, 5-(2-methylpropyl)-1-methyl-1-cyclohexene, 1-methylidene-3-(2-methylpropyl)cyclohexane, and myrcene.

Very generally, the compound of formula (I) as contemplated herein can be used for example to release the following fragrance alcohols and fragrance phenols: amyl alcohol; hexyl alcohol; 2-hexyl alcohol; heptyl alcohol; octyl alcohol; nonyl alcohol; decyl alcohol; undecyl alcohol; lauryl alcohol; myristyl alcohol; 3-methylbut-2-en-1-ol; 3-methyl-1-pentanol; cis-3-hexenol; cis-4-hexenol; 3,5,5-trimethyl-hexanol; 3,4,5,6,6-pentamethylheptan-2-ol; citronellol; geraniol; oct-1-en-3-ol; 2,5,7-trimethyloctan-3-ol; 2-cis-3,7-dimethyl-2,6-octadien-1-ol; 6-ethyl-3-methyl-5-octen-1-ol; 3,7-dimethyloct-3,6-dienol; 3,7-dimethyloctanol; 7-methoxy-3,7-dimethyloctan-2-ol; cis-6-nonenol; 5-ethyl-2-nonanol; 6,8-dimethyl-2-nonanol; 2,2,8-trimethyl-7(8)-nonen-3-ol; nona-2,6-dien-1-ol; 4-methyl-3-decen-5-ol; dec-9-en-1-ol; benzyl alcohol; 2-methylundecanol; 10-undecen-1-ol; 1-phenylethanol; 2-phenylethanol; 2-methyl-3-phenyl-3-propenol; 2-phenylpropanol; 3-phenylpropanol; 4-phenyl-2-butanol; 2-methyl-5-phenylpentanol; 2-methyl-4-phenylpentanol; 3-methyl-5-phenylpentanol; 2-(2-methylphenyl)ethanol; 4-(1-methylethyl)benzene; methanol; 4-(4-hydroxyphenyl)butan-2-one; 2-phenoxyethanol; 4-(1-methylethyl)-2-hydroxy-1-methylbenzene; 2-methoxy-4-methylphenol; 4-methylphenol; anise alcohol; p-tolyl alcohol; cinnamic alcohol; vanillin; ethyl vanillin; eugenol; isoeugenol; thymol; anethole; decahydro-2-naphthol; borneol; cedrenol; farnesol; fenchyl alcohol; menthol; 3,7,11-trimethyl-2,6,10-dodecatrien-1-ol; alpha-ionol; tetra-ionol; 2-(1,1-dimethylethyl)cyclohexanol; 3-(1,1-dimethylethyl)cyclohexanol; 4-(1,1-dimethylethyl)cyclohexanol; 4-isopropylcyclohexanol; 6,6-dimethylbicyclo[3.3.1]hept-2-ene-2-ethanol; 6,6-dimethylbicyclo[3.1.1]hept-2-enemethanol; p-menth-8-en-3-ol; 3,3,5-trimethylcyclohexanol; 2,4,6-trimethyl-3-cyclohexenylmethanol; 4-(1-methylethyl)cyclohexanemethanol; 4-(1,1-dimethylethyl)cyclohexanol; 2-(1,1-dimethylethyl)cyclohexanol; 2,2,6-trimethyl-alpha-propylcyclohexanepropanol, 5-(2,2,3-trimethyl-3-cyclopentenyl)-3-methylpentan-2-ol; 3-methyl-5-(2,2,3-trimethylcyclopentyl-3-enyl)pent-4-en-2-ol; 2-ethyl-4-(2,2,3-trimethylcyclopentyl-3-enyl)but-2-en-1-ol; 4-(5,5,6-trimethylbicyclo[2.2.1]hept-2-yl)cyclohexanol; 2-(2-methylpropyl)-4-hydroxy-4-methyltetrahydropyran; 2-cyclohexylpropanol; 2-(1,1-dimethylethyl)-4-methylcyclohexanol; 1-(2-tert-butylcyclohexyloxy)-2-butanol; 1-(4-isopropylcyclohexyl)ethanol; 1-(4-hydroxyphenyl)butan-3-one; 2,6-dimethyloct-7-en-2-ol; 2,6-dimethylheptan-2-ol; 3,7-dimethylocta-1,6-dien-3-ol.

In a further embodiment, the compound as contemplated herein is a compound according to the following formula (II)

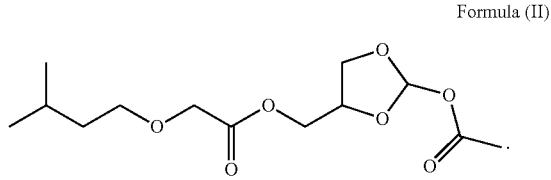 [SMILES: CC(=O)OC1OCC(COC(=O)COCCC(C)C)O1]

Formula (II)

The compounds as contemplated herein can be incorporated in a stable manner in the customary detergent or cleaning agent matrices, in cosmetics and existing fragrance compositions. They enable an immediate but also a delayed release of the stored fragrance alcohols and fragrance alkenes. One preferred fragrance is allyl isoamyl glycolate. These fragrances give customary detergents or cleaning agents and cosmetics a particularly long-lasting freshness impression. In particular, the dried, washed textile benefits from the good long-term freshness fragrance effect. The slow release of the stored fragrance takes place under the effect of Brønsted and/or Lewis acids. The effect of Brønsted acids is advantageous.

A further subject matter of the present disclosure is a detergent or cleaning agent, preferably a detergent, softener or washing auxiliary, containing at least one compound of formula (I). In various embodiments, said compound is contained in amounts between about 0.0001 and about 5% by weight, advantageously between about 0.001 and about 4% by weight, more advantageously between about 0.005 and about 3% by weight, in particular between about 0.01 and about 2% by weight, in each case based on the total agent. Suitable cleaning agents are for example cleaning agents for hard surfaces, such as preferably dishwashing agents. They may also be cleaning agents such as, for example, household cleaners, all-purpose cleaners, window cleaners, floor cleaners, etc. It may preferably be a product for cleaning toilet bowls and urinals, advantageously a flush-action cleaner for hanging in the toilet bowl.

According to one preferred embodiment as contemplated herein, the detergent or cleaning agent as contemplated herein contains at least one surfactant selected from anionic, cationic, nonionic, zwitterionic, amphoteric surfactants, or mixtures thereof.

According to another preferred embodiment as contemplated herein, the agent as contemplated herein is in solid or liquid form.

A further subject matter as contemplated herein is a cosmetic agent containing at least one compound according to formula (I) containing the compound preferably in amounts between about 0.0001 and about 50% by weight, advantageously between about 0.001 and about 5% by weight, more advantageously between about 0.005 and about 3% by weight, in particular between about 0.01 and about 2% by weight, in each case based on the total agent.

A further subject matter as contemplated herein is an air freshening product (for example room air freshener, room deodorant, room spray, etc.) containing at least one compound according to formula (I), wherein the compound of formula (I) is contained preferably in amounts between about 0.0001 and about 50% by weight, more preferably between about 0.001 and about 5% by weight, yet more preferably between about 0.01 and about 3% by weight, most preferably between about 0.1 and about 2% by weight, in each case based on the total weight of the agent.

According to another preferred embodiment as contemplated herein, additional fragrances are contained in an agent as contemplated herein (that is to say a detergent or cleaning agent, cosmetic agent or air freshening product), said additional fragrances being selected in particular from the group comprising fragrances of natural or synthetic origin, preferably readily volatile fragrances, higher-boiling fragrances, solid fragrances and/or adherent fragrances.

Adherent odorants which can be used with advantage in the context of the present disclosure are for example essential oils such as *angelica* root oil, anise oil, *arnica* flower oil, basil oil, bay oil, bergamot oil, champaca flower oil, silver fir oil, silver fir cone oil, elemi oil, *eucalyptus* oil, fennel oil, fir needle oil, *galbanum* oil, geranium oil, ginger grass oil, guaiac wood oil, gurjun balsam oil, helichrysum oil, ho oil, ginger oil, iris oil, cajeput oil, calamus oil, chamomile oil, camphor oil, *cananga* oil, cardamom oil, *cassia* oil, pine needle oil, copaiva balsam oil, coriander oil, spearmint oil, caraway oil, cumin oil, lavender oil, lemon grass oil, lime oil, mandarin oil, melissa oil, musk seed oil, myrrh oil, clove oil, neroli oil, niaouli oil, olibanum oil, orange oil, oregano oil, palmarosa oil, patchouli oil, balsam Peru oil, petitgrain oil, pepper oil, peppermint oil, pimento oil, pine oil, rose oil, rosemary oil, sandalwood oil, celery oil, spike lavender oil, star anise oil, turpentine oil, *thuja* oil, thyme oil, *verbena* oil, vetiver oil, juniper berry oil, wormwood oil, wintergreen oil, ylang-ylang oil, hyssop oil, cinnamon oil, cinnamon leaf oil, citronella oil, lemon oil and cypress oil.

However, in the context of the present disclosure, higher-boiling or solid odorants of natural or synthetic origin can also be used as adherent odorants or odorant mixtures, that is to say fragrances. These compounds include the compounds mentioned below, as well as mixtures thereof: ambrettolide, alpha-amyl cinnamaldehyde, anethole, anisaldehyde, anisyl alcohol, anisole, methyl anthranilate, acetophenone, benzyl acetone, benzaldehyde, ethyl benzoate, benzophenone, benzyl alcohol, benzyl acetate, benzyl benzoate, benzyl formate, benzyl valerate, bomeol, bornyl acetate, alpha-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, methyl heptynecarboxylate, heptaldehyde, hydroquinone dimethyl ether, hydroxycinnamaldehyde, hydroxycinnamyl alcohol, indole, irone, isoeugenol, isoeugenol methyl ether, isosafrole, jasmone, camphor, carvacrol, carvone, p-cresol methyl ether, coumarin, p-methoxyacetophenone, methyl n-amyl ketone, dimethyl anthranilate, p-methylacetophenone, methyl chavicol, p-methylquinoline, methyl beta-naphthyl ketone, methyl-n-nonyl acetaldehyde, methyl n-nonyl ketone, muscone, beta-naphthol ethyl ether, beta-naphthol methyl ether, nerol, nitrobenzene, n-nonyl aldehyde, nonyl alcohol, n-octyl aldehyde, p-oxyacetophenone, pentadecanolide, beta-phenylethyl alcohol, phenylacetaldehyde dimethyl acetal, phenylacetic acid, pulegone, safrole, isoamyl salicylate, methyl salicylate, hexyl salicylate, cyclohexyl salicylate, santalol,e skatole, terpineol, thymene, thymol, gamma-undecalactone, vanillin, veratrum aldehyde, cinnamaldehyde, cinnamyl alcohol, cinnamic acid, ethyl cinnamate, benzyl cinnamate. The more readily volatile fragrances include in particular the lower-boiling odorants of natural or synthetic origin, which can be used alone or in mixtures. Examples of readily volatile fragrances are alkyl isothiocyanates (alkyl mustard oils), butanedione, limonene, linalool, linalyl acetate and propionate, menthol, menthone, methyl n-heptenone, phellandrene, phenylacetaldehyde, terpinyl acetate, citral, citronellal.

According to another preferred embodiment, the agent as contemplated herein (that is to say detergent or cleaning agent, cosmetic agent or air freshening product) has at least one active component, preferably a plurality of active components, in particular components having washing, care or cleaning activity and/or cosmetic components, advantageously selected from the group comprising anionic surfactants, cationic surfactants, amphoteric surfactants, nonionic surfactants, acidifying agents, alkalizing agents, anti-wrinkle agents, antibacterial substances, antioxidants, anti-redeposition agents, antistatic agents, builder substances, bleaching agents, bleach activators, bleach stabilizers, bleach catalysts, ironing aids, co-builders, fragrances, shrinkage preventers, electrolytes, enzymes, color protectants, coloring agents, dyes, dye transfer inhibitors, fluorescing agents, fungicides, germicides, odor-complexing substances, auxiliaries, hydrotropes, clear rinsers, complexing agents, preservatives, corrosion inhibitors, water-miscible organic solvents, optical brighteners, perfumes, perfume carriers, pearlescent agents, pH adjusting agents, proofing and impregnating agents, polymers, swelling and anti-slip agents, foam inhibitors, phyllosilicates, soil-repelling substances, protection agents, silicone oils, soil-release active ingredients, UV-protection substances, viscosity regulators, thickening agents, discoloration inhibitors, graying inhibitors, vitamins and/or softeners. As contemplated herein, unless otherwise indicated, amounts indicated in % by weight refer to the total weight of the agent as contemplated herein.

The amounts of the individual ingredients in the agents as contemplated herein (that is to say detergent or cleaning agent, cosmetic agent or air freshening product) are guided in each case by the intended use of the agents in question, and a person skilled in the art is in principle familiar with the orders of magnitude of the amounts of the ingredients to be used or can find these in the associated technical literature. Depending on the intended use of the agents as contemplated herein, the surfactant content for example will be selected to be higher or lower. Usually, for example, the surfactant content of detergents can be between about 10 and about 50% by weight, preferably between about 12.5 and about 30% by weight and in particular between about 15 and about 25% by weight, whereas for example cleaning agents for automatic dishwashing can contain for example between about 0.1 and about 10% by weight, preferably between about 0.5 and about 7.5% by weight and in particular between about 1 and about 5% by weight surfactants.

The agents as contemplated herein (that is to say detergent or cleaning agent, cosmetic agent or air freshening product) may contain surfactants, suitable surfactants being preferably anionic surfactants, nonionic surfactants and mixtures thereof, but also cationic surfactants. Suitable nonionic surfactants are in particular ethoxylation and/or propoxylation products of alkyl glycosides and/or linear or branched alcohols having in each case 12 to 18 carbon atoms in the alkyl moiety and 3 to 20, preferably 4 to 10 alkyl ether groups. Use can also be made of corresponding ethoxylation and/or propoxylation products of N-alkylamines, vicinal diols, fatty acid esters and fatty acid amides, which in terms of the alkyl moiety correspond to the aforementioned long-chain alcohol derivatives, and also of alkylphenols having 5 to 12 carbon atoms in the alkyl residue.

Suitable anionic surfactants are in particular soaps, and those which contain sulfate or sulfonate groups with preferably alkali ions as cations. Soaps which can be used are preferably the alkali salts of saturated or unsaturated fatty acids having 12 to 18 carbon atoms. Such fatty acids can also be used in not fully neutralized form. The surfactants of the sulfate type which can be used include the salts of the sulfuric acid semiesters of fatty alcohols having 12 to 18 carbon atoms, and the sulfation products of the aforementioned nonionic surfactants having a low degree of ethoxylation. The surfactants of the sulfonate type which can be used include linear alkylbenzenesulfonates having 9 to 14 carbon atoms in the alkyl moiety, alkanesulfonates having 12 to 18 carbon atoms, and olefin sulfonates having 12 to 18 carbon atoms which are produced in the reaction of corresponding monoolefins with sulfur trioxide, as well as alpha-sulfo fatty acid esters which are produced in the sulfonation of fatty acid methyl or ethyl esters.

Cationic surfactants are preferably selected from among the esterquats and/or the quaternary ammonium compounds (QACs) according to the general formula $(R^I)(R^{II})(R^{III})(R^{IV})N^+X^-$, in which $R^I$ to $R^{IV}$ denote identical or different $C_{1-22}$ alkyl residues, $C_{7-28}$ arylalkyl residues or heterocyclic residues, wherein two or, in the case of an aromatic bond such as in pyridine, even three residues together with the nitrogen atom form the heterocycle, for example a pyridinium or imidazolinium compound, and $X^-$ denotes halide ions, sulfate ions, hydroxide ions or similar anions. QACs can be produced by reacting tertiary amines with alkylating agents, such as for example methyl chloride, benzyl chloride, dimethyl sulfate, dodecyl bromide, but also ethylene oxide. The alkylation of tertiary amines with a long alkyl residue and two methyl groups can be achieved particularly easily, and the quaternization of tertiary amines with two long residues and a methyl group can also be carried out using methyl chloride under mild conditions. Amines which have three long alkyl residues or hydroxy-substituted alkyl residues have low reactivity and are quaternized for example using dimethyl sulfate. Suitable QACs are for example benzalkonium chloride (N-alkyl-N,N-dimethylbenzylammonium chloride), Benzalkon B (m,p-dichlorobenzyldimethyl-$C_{12}$-alkylammonium chloride), benzoxonium chloride (benzyldodecyl-bis(2-hydroxyethyl)ammonium chloride), cetrimonium bromide (N-hexadecyl-N,N-trimethylammonium bromide), benzethonium chloride (N,N-dimethyl-N-[2-[2-[p-(1,1,3,3-tetramethylbutyl)phenoxy]ethoxy]ethyl] benzylammonium chloride), dialkyldimethylammonium chlorides, such as di-n-decyldimethylammonium chloride, didecyldimethylammonium bromide, dioctyldimethylammonium chloride, 1-cetylpyridinium chloride and thiazoline iodide, and mixtures thereof. Preferred QACs are the benzalkonium chlorides having $C_8$-$C_{22}$ alkyl residues, in particular $C_{12}$-$C_{14}$ alkylbenzyldimethylammonium chloride.

Preferred esterquats are methyl-N-(2-hydroxyethyl)-N,N-di(tallow-acyloxyethyl)ammonium methosulfate, bis(palmitoyl)ethylhydroxyethylmethylammonium methosulfate or methyl-N,N-bis(acyloxyethyl)-N-(2-hydroxyethyl)ammonium methosulfate. Commercially available examples are the methylhydroxyalkyldialkoyloxyalkylammonium methosulfates marketed by the company Stepan under the brand name Stepantex® or the products from the company BASF SE known under the trade name Dehyquart or the products from the manufacturer Evonik known under the name Rewoquat.

Surfactants are contained in the agents as contemplated herein (that is to say detergent or cleaning agent, cosmetic agent or air freshening product) in quantitative proportions of preferably from about 5% by weight to about 50% by weight, in particular from about 8% by weight to about 30% by weight. Particularly in laundry post-treatment agents, preferably up to about 30% by weight, in particular about 5% by weight to about 15% by weight surfactants are used, among these preferably at least a proportion of cationic surfactants.

An agent as contemplated herein, in particular a detergent or cleaning agent, preferably contains at least one water-soluble and/or water-insoluble, organic and/or inorganic builder. The water-soluble organic builder substances include polycarboxylic acids, in particular citric acid and sugar acids, monomeric and polymeric aminopolycarboxylic acids, in particular methylglycinediacetic acid, nitrilotriacetic acid and ethylenediaminetetraacetic acid as well as polyaspartic acid, polyphosphonic acids, in particular aminotris(methylenephosphonic acid), ethylenediaminetetrakis (methylenephosphonic acid) and 1-hydroxyethane-1,1-diphosphonic acid, polymeric hydroxy compounds, such as dextrin, and polymeric (poly)carboxylic acids, polymeric acrylic acids, methacrylic acids, maleic acids and copolymers of these, which can also contain, polymerized into them, small proportions of polymerizable substances without carboxylic acid functionality. Suitable, although less preferred, compounds from this class are copolymers of acrylic acid or methacrylic acid with vinyl ethers, such as vinyl methyl ethers, vinyl esters, ethylene, propylene and styrene, in which the proportion of acid is at least about 50% by weight. Particularly for preparing liquid agents, the organic builder substances can be used in the form of aqueous solutions, preferably in the form of about 30 to about 50% by weight aqueous solutions. All the aforementioned acids are generally used in the form of their water-soluble salts, in particular their alkali salts.

Organic builder substances can, if desired, be contained in amounts up to about 40% by weight, in particular up to about 25% by weight and preferably from about 1% by weight to about 8% by weight. Amounts close to the aforementioned upper limit are preferably used in paste-like or liquid, in particular aqueous, agents as contemplated herein. Laundry post-treatment agents as contemplated herein, such as for example softeners, may optionally also be free from organic builder.

Suitable water-soluble inorganic builder materials are in particular alkali silicates and polyphosphates, preferably sodium triphosphate. As water-insoluble, water-dispersible inorganic builder materials, use may be made in particular of crystalline or amorphous alkali aluminosilicates, if desired, in amounts of up to about 50% by weight, preferably not above about 40% by weight, and in liquid agents in particular from about 1% by weight to about 5% by weight. Among these, preference is given to the crystalline sodium aluminosilicates in detergent quality, in particular zeolite A, P and optionally X. Amounts close to the aforementioned upper limit are preferably used in solid, particulate agents. Suitable aluminosilicates have in particular no particles having a particle size above about 30 µm and consist in a proportion of at least about 80% by weight of particles having a size below about 10 µm.

Suitable substitutes or partial substitutes for the aforementioned aluminosilicate are crystalline alkali silicates which may be present alone or in a mixture with amorphous silicates. The alkali silicates which can be used as builders in the agents as contemplated herein preferably have a molar ratio of alkali oxide to $SiO_2$ of less than about 0.95, in particular from about 1:1.1 to about 1:12, and may be in amorphous or crystalline form. Preferred alkali silicates are the sodium silicates, in particular the amorphous sodium silicates, with a molar ratio $Na_2O:SiO_2$ of from about 1:2 to about 1:2.8. As crystalline silicates which may be used alone or in a mixture with amorphous silicates, use is preferably made of crystalline phyllosilicates of general formula $Na_2Si_xO_{2x+1} \cdot yH_2O$, in which x, the so-called modulus, is a number from about 1.9 to about 4 and y is a number from 0 to 20, and preferred values for x are 2, 3 or 4. Preferred crystalline phyllosilicates are those in which x in the aforementioned general formula assumes the value 2 or 3. In particular, both beta- and delta-sodium disilicates ($Na_2Si_2O_5 \cdot yH_2O$) are preferred. Practically anhydrous crystalline alkali silicates of the aforementioned general formula, which are produced from amorphous alkali silicates and in which x is a number from about 1.9 to about 2.1, can also be used in agents as contemplated herein. In another preferred embodiment of agents as contemplated herein, use is made of a crystalline sodium phyllosilicate having a modulus of 2 to 3, as can be produced from sand and soda. Crystalline sodium silicates having a modulus in the range from about 1.9 to about 3.5 are used in another preferred embodiment of agents as contemplated herein. If alkali aluminosilicate, in particular zeolite, is also present as an additional builder substance, the weight ratio of aluminosilicate to silicate, in each case based on anhydrous active substances, is preferably about 1:10 to about 10:1. In agents which contain both amorphous and crystalline alkali silicates, the weight ratio of amorphous alkali silicate to crystalline alkali silicate is preferably about 1:2 to about 2:1 and in particular about 1:1 to about 2:1.

Builder substances are, if desired, contained in the agents as contemplated herein in amounts of up to about 60% by weight, in particular from about 5% by weight to about 40% by weight. Laundry post-treatment agents as contemplated herein, such as for example softeners, are preferably free from inorganic builder.

Suitable peroxygen compounds are in particular organic peracids or peracid salts of organic acids, such as phthalimidoperoxycaproic acid, peroxybenzoic acid, or salts of diperoxydodecanedioic acid, hydrogen peroxide and inorganic salts which release hydrogen peroxide under the use conditions, such as perborate, percarbonate and/or persilicate. If solid peroxygen compounds are to be used, these may be used in the form of powders or granules, which may also be coated in a manner known in principle. With particular preference, use is optionally made of alkali percarbonate, alkali perborate monohydrate or, particularly in liquid agents, hydrogen peroxide in the form of aqueous solutions which contain from about 3% by weight to about 10% by weight hydrogen peroxide. If an agent as contemplated herein contains bleaching agents, such as preferably peroxygen compounds, these are present in amounts of preferably up to about 50% by weight, in particular from 5% by weight to about 30% by weight. The addition of small amounts of known bleaching agent stabilizers, such as for example phosphonates, borates or metaborates and metasilicates, as well as magnesium salts such as magnesium sulfate, may be useful.

As bleach activators, use may be made of compounds which under perhydrolysis conditions form aliphatic peroxocarboxylic acids having preferably 1 to 10 carbon atoms, in particular 2 to 4 carbon atoms, and/or optionally substituted perbenzoic acid. Substances which carry O— and/or N-acyl groups with the aforementioned number of carbon atoms and/or optionally substituted benzoyl groups are suitable. Preference is given to polyacylated alkylenediamines, in particular tetraacetyl ethylenediamine (TAED), acylated triazine derivatives, in particular 1,5-diacetyl-2,4-dioxohexahydro-1,3,5-triazine (DADHT), acylated glycolurils, in particular tetraacetyl glycoluril (TAGU), N-acylimides, in particular N-nonanoyl succinimide (NOSI), acylated phenol sulfonates, in particular n-nonanoyl or isononanoyl oxybenzenesulfonate (n- or iso-NOBS), carboxylic anhydrides, in particular phthalic anhydride, acylated polyhydric alcohols, in particular triacetin, ethylene glycol diacetate, 2,5-diacetoxy-2,5-dihydrofuran and enol esters as well as acetylated sorbitol and mannitol and mixtures thereof (SORMAN), acylated sugar derivatives, in particular pentaacetyl glucose (PAG), pentaacetyl fructose, tetraacetyl xylose and octaacetyl lactose as well as acetylated, optionally N-alkylated glucamine and gluconolactone, and/or N-acylated lactams, for example N-benzoyl caprolactam. Hydrophile-substituted acyl acetals and acyl lactams are also used with preference. Combinations of conventional bleach activators can also be used. Such bleach activators may be contained in the usual quantitative range, preferably in amounts of from about 1% by weight to about 10% by weight, in particular from about 2% by weight to about 8% by weight, based on the total agent.

In addition to the conventional bleach activators mentioned above, or in place thereof, sulfonimines and/or bleach-boosting transition metal salts or transition metal complexes may also be contained as so-called bleach catalysts.

Suitable enzymes which can be used in the agents are those from the class of the proteases, cutinases, amylases, pullulanases, hemicellulases, cellulases, lipases, oxidases and peroxidases, as well as mixtures thereof. Enzymatic active ingredients obtained from fungi or bacteria, such as *Bacillus subtilis, Bacillus licheniformis, Streptomyces griseus, Humicola lanuginosa, Humicola insolens, Pseudomonas pseudoalcaligenes* or *Pseudomonas cepacia*, are particularly suitable. The optionally used enzymes may be adsorbed onto carrier substances and/or embedded in encapsulating substances in order to protect them against premature inactivation. If desired, they are contained in the agents as contemplated herein preferably in amounts no greater than about 5% by weight, in particular from about 0.2% by weight to about 2% by weight.

The agents may optionally also contain, as optical brighteners, for example derivatives of diaminostilbenedisulfonic acid or alkali metal salts thereof. Salts of 4,4'-bis(2-anilino-4-morpholino-1,3,5-triazinyl-6-amino)stilbene-2,2'-disulfonic acid or compounds of similar structure which carry in place of the morpholino group a diethanolamino group, a methylamino group, an anilino group or a 2-methoxyethylamino group are suitable for example.

Suitable foam inhibitors include for example organopolysiloxanes and mixtures thereof with microfine, optionally silanized silica as well as paraffin waxes and mixtures thereof with silanized silica or bis-fatty acid alkylenediamides. Mixtures of different foam inhibitors are also used with advantage, for example mixtures of silicones, paraffins or waxes. The foam inhibitors, in particular silicone- and/or paraffin-containing foam inhibitors, are preferably bound to a granular carrier substance which is soluble or dispersible in water. Particular preference is given to mixtures of paraffin waxes and bistearylethylenediamides.

In addition, the agents may also contain components which positively influence the washability of oil and fat from textiles, so-called soil release active ingredients. This effect becomes particularly clear when a textile which has already been washed multiple times beforehand with an agent as contemplated herein containing said oil- and fat-dissolving component becomes soiled. The preferred oil- and fat-dissolving components include for example nonionic cellulose ethers such as methyl cellulose and methyl hydroxypropyl cellulose having a proportion of methoxyl groups of from about 15 to about 30% by weight and hydroxypropoxyl groups of from about 1 to about 15% by weight, in each case based on the nonionic cellulose ether, and also the polymers, known from the prior art, of phthalic acid and/or terephthalic acid or derivatives thereof with monomeric and/or polymeric diols, in particular polymers of ethylene terephthalates and/or polyethylene glycol terephthalates or anionically and/or nonionically modified derivatives thereof.

The agents may also contain color transfer inhibitors, preferably in amounts of from about 0.1% by weight to about 2% by weight, in particular from about 0.1% by weight to about 1% by weight, which in one preferred embodiment as contemplated herein are polymers of vinylpyrrolidone, vinylimidazole, vinylpyridine N-oxide or copolymers thereof.

Graying inhibitors have the task of keeping suspended in the liquor the dirt that has been detached from the textile fiber. Suitable for this purpose are water-soluble colloids usually of organic nature, for example starch, sizing material, gelatin, salts of ether carboxylic acids or ether sulfonic acids of starch or cellulose or salts of acidic sulfuric acid esters of cellulose or of starch. Water-soluble polyamides containing acidic groups are also suitable for this purpose. Use can also be made of starch derivatives other than those mentioned above, for example aldehyde starches. Use can preferably be made of cellulose ethers, such as carboxymethyl cellulose (Na salt), methyl cellulose, hydroxyalkyl cellulose and mixed ethers, such as methyl hydroxyethyl cellulose, methyl hydroxypropyl cellulose, methyl carboxymethyl cellulose and mixtures thereof, for example in amounts of from about 0.1 to about 5% by weight, based on the agent.

The organic solvents which can be used in the agents as contemplated herein, particularly when the latter are in liquid or paste-like form, include alcohols having 1 to 4 carbon atoms, in particular methanol, ethanol, isopropanol and tert-butanol, diols having 2 to 4 carbon atoms, in particular ethylene glycol and propylene glycol, as well as mixtures thereof and the ethers which can be derived from the aforementioned compound classes. Such water-miscible solvents are present in the agents as contemplated herein preferably in amounts of no greater than 30% by weight, in particular from about 6% by weight to about 20% by weight.

To set a desired pH which does not result by itself from the mixing of the other components, the agents as contemplated herein may contain acids which are safe for the system and for the environment, in particular citric acid, acetic acid, tartaric acid, malic acid, lactic acid, glycolic acid, succinic acid, glutaric acid and/or adipic acid, but also mineral acids, in particular sulfuric acid, or bases, in particular ammonium or alkali hydroxides. Such pH regulators are optionally contained in the agents as contemplated herein, preferably no greater than about 20% by weight, in particular from about 1.2% by weight to about 17% by weight.

The preparation of solid agents as contemplated herein (that is to say in particular detergents or cleaning agents) presents no difficulties and may take place in a manner known in principle, for example by spray drying or granulation, wherein optional peroxygen compound and optional bleach catalyst are added later if desired. In order to prepare agents as contemplated herein with an increased bulk weight, in particular in the range from about 650 g/l to about 950 g/l, preference is given to a method which comprises an extrusion step. The preparation of liquid agents as contemplated herein likewise presents no difficulties and can likewise take place in a known manner.

The preparation of the compounds of formula (I) as contemplated herein will be described by way of example in the Examples section with reference to the preparation of a fragrance storage substance containing citronellol and geraniol. The other compounds of general formula (I) and in particular the compounds of formulae (II) to (XIII) can also be obtained via this basic synthesis route.

According to one preferred embodiment, the teaching as contemplated herein can be used to significantly reduce the proportion of perfume in detergents, cleaning agents and body care agents. As a result, it is possible to offer perfumed products even for those particularly sensitive consumers who, because of specific intolerances and irritations, can use normally perfumed products only to a limited extent or not at all.

In various embodiments of the present disclosure, the detergents or cleaning agents are in liquid or solid form.

A preferred solid, in particular powdered, detergent as contemplated herein may contain, besides the compound as contemplated herein, in particular also components which are selected for example from the following:

- anionic surfactants, such as preferably alkylbenzene sulfonate, alkyl sulfate, for example in amounts of preferably from about 5 to about 30% by weight,
- nonionic surfactants, such as preferably fatty alcohol polyglycol ether, alkyl polyglucoside, fatty acid glucamide, for example in amounts of preferably from 0.5 to 15% by weight,
- builders, such as for example zeolite, polycarboxylate, sodium citrate, in amounts of for example from 0 to about 70% by weight, advantageously from about 5 to about 60% by weight, preferably from about 10 to about 55% by weight, in particular from about 15 to about 40% by weight,
- alkalis, such as for example sodium carbonate, in amounts of for example from 0 to 35% by weight, advantageously from about 1 to about 30% by weight, preferably from about 2 to about 25% by weight, in particular from about 5 to about 20% by weight,
- bleaching agents, such as for example sodium perborate, sodium percarbonate, in amounts of for example from 0 to about 30% by weight, advantageously from about 5 to about 25% by weight, preferably from about 10 to about 20% by weight, corrosion inhibitors, for example sodium silicate, in amounts of for example from 0 to about 10% by weight, advantageously from about 1 to about 6% by weight, preferably from about 2 to about 5% by weight, in particular from about 3 to about 4% by weight, stabilizers, for example phosphonates, advantageously from 0 to about 1% by weight, foam inhibitor, for example soap, silicone oils, paraffins, advantageously from 0 to about 4% by weight, preferably from about 0.1 to about 3% by weight, in particular from about 0.2 to about 1% by weight, enzymes, for example proteases, amylases, cellulases, lipases, advantageously from 0 to about 2% by weight, preferably from about 0.2 to about 1% by weight, in particular from about 0.3 to about 0.8% by weight, graying inhibitor, for example carboxymethyl cellulose, advantageously from 0 to about 1% by weight, discoloration inhibitor, for example polyvinylpyrrolidone derivatives, preferably from 0 to about 2% by weight, adjusting agents, for example sodium sulfate, advantageously from 0 to about 20% by weight, optical brighteners, for example stilbene derivative, biphenyl derivative, advantageously from 0 to about 0.4% by weight, in particular from about 0.1 to about 0.3% by weight, optionally further fragrances, optionally water, optionally soap, optionally bleach activators, optionally cellulose derivatives, optionally soil repellents, the % by weight in each case being based on the total agent.

In another preferred embodiment as contemplated herein, the agent is in liquid form, preferably in gel form. Preferred liquid detergents or cleaning agents and cosmetics have water contents of for example from about 10 to about 95% by weight, preferably from about 20 to about 80% by weight and in particular from about 30 to about 70% by weight, based on the total agent. In the case of liquid concentrates, the water content may also be particularly low, for example less than about 30% by weight, preferably less than about 20% by weight, in particular less than about 15% by weight, the % by weight in each case being based on the total agent. The liquid agents may also contain nonaqueous solvents.

A preferred liquid, in particular gel-like, detergent as contemplated herein may contain, besides the compound as contemplated herein, in particular also components which are selected for example from the following:

anionic surfactants, such as preferably alkylbenzene sulfonate, alkyl sulfate, for example in amounts of preferably from about 5 to about 40% by weight, nonionic surfactants, such as preferably fatty alcohol polyglycol ether, alkyl polyglucoside, fatty acid glucamide, for example in amounts of preferably from about 0.5 to about 25% by weight, builders, such as for example zeolite, polycarboxylate, sodium citrate, advantageously from 0 to about 15% by weight, preferably from about 0.01 to about 10% by weight, in particular from about 0.1 to about 5% by weight, foam inhibitor, for example soap, silicone oils, paraffins, in amounts of for example from 0 to about 10% by weight, advantageously from about 0.1 to about 4% by weight, preferably from about 0.2 to about 2% by weight, in particular from about 1 to about 3% by weight, enzymes, for example proteases, amylases, cellulases, lipases, in amounts of for example from 0 to about 3% by weight, advantageously from about 0.1 to about 2% by weight, preferably from about 0.2 to about 1% by weight, in particular from about 0.3 to about 0.8% by weight, optical brighteners, for example stilbene derivative, biphenyl derivative, in amounts of for example from 0 to about 1% by weight, advantageously from about 0.1 to about 0.3% by weight, in particular from about 0.1 to about 0.4% by weight, optionally further fragrances, optionally stabilizers, water, optionally soap, in amounts of for example from 0 to about 25% by weight, advantageously from about 1 to about 20% by weight, preferably from about 2 to about 15% by weight, in particular from about 5 to about 10% by weight, optionally solvents (preferably alcohols), advantageously from 0 to about 25% by weight, preferably from about 1 to about 20% by weight, in particular from about 2 to about 15% by weight, the % by weight in each case being based on the total agent.

A preferred liquid softener as contemplated herein may contain, besides the ketone as contemplated herein, in particular also components which are selected from the following:

cationic surfactants, such as in particular esterquats, for example in amounts of from about 5 to about 30% by weight, co-surfactants, such as for example glycerol monostearate, stearic acid, fatty alcohols, fatty alcohol ethoxylates, for example in amounts of from 0 to about 5% by weight, preferably from about 0.1 to about 4% by weight, emulsifiers, such as for example fatty amine ethoxylates, for example in amounts of from 0 to about 4% by weight, preferably from about 0.1 to about 3% by weight, optionally further fragrances, dyes, preferably in the ppm range, stabilizers, preferably in the ppm range, solvents, such as for example water, in amounts of preferably from about 60 to about 90% by weight, the % by weight in each case being based on the total agent.

A further subject matter as contemplated herein is a method for fragrancing surfaces, wherein a compound of formula (I) as contemplated herein or a detergent or cleaning agent, cosmetic agent or air freshening product as contemplated herein is applied to the surface to be fragranced (for example textile, dishes, floor) and the compound or the agent then (i) is heated to a temperature of from about 20° C. to about 250° C., preferably from about 20° C. to about 90° C., and/or (ii) is brought into contact with a Lewis acid and/or Brønsted acid, preferably with a Brønsted acid.

As contemplated herein, in particular the acidic protective film (hydrolipid film) of the skin, which is formed mainly by secretions of the skin, such as sweat and fatty acids, and sets a pH of around about 4 to about 7 on the skin, is suitable for the acid-induced release of the stored fragrances. Said protective film brings about a delayed release of the fragrances as described herein, for example when the compound of formula (I) is applied to a textile which is brought into contact with said protective film.

All embodiments which have been described herein in connection with the compounds of formula (I) are applicable in the same way also to the described agents, methods and uses, and vice versa. Further embodiments can be found in the following examples, but the disclosure is not limited thereto.

EXAMPLES

Example 1

1-(4-Ethoxy-1,3-dioxolan-2-yl)-3-(3-methylbutoxy)propan-2-one

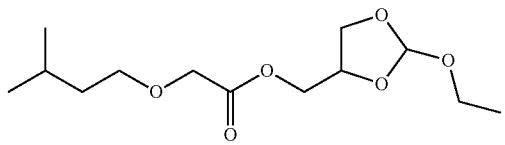 [SMILES: CCOC1OCC(COC(=O)COCCC(C)C)O1]

5.0 g (22.7 mmol) of 2,3-dihydroxypropyl 2-(isopentyloxy)acetate were placed in a 100 ml round-bottomed flask together with 4.4 g (29.5 mmol) of triethyl orthoformate. 2 drops of acetic acid were added as catalyst. The solution was then heated to 100° C. and the alcohol liberated was distilled off. The residue was extracted with sodium hydrogen carbonate and diethyl ether, dried with anhydrous sodium sulfate, and the solvent was removed under reduced pressure.

Yield: 5 g (19.09 mmol), 80%

The crude product is purified by ball tube distillation (bp. 135° C., 1×10$^{-3}$ bar).

Alternatively, the product can be obtained by column chromatography on silica gel (n-hexane:ethyl acetate=1.2, Rf=0.74).

$^1$H-NMR (600 MHz, CDCl$_3$): d=0.91 (d, J=6.7 Hz, 6H), 1.23 (t, J=7.1 Hz, 3H), 1.48-1.56 (q, J=6.8 Hz, 2H), 1.62-1.79 (m, 1H), 3.53-3.63 (m, 4H), 3.81 (dddd, J=5.1, 6.8, 8.1, 8.1 Hz), 4.11 (s, 2H), 4.13-4.57 (m, 4H), 5.83 and 5.85 (s and s, 1H).

$^{13}$C-NMR (150 MHz, CDCl$_3$): d=15.0 (CH$_3$), 22.4 (2×CH$_3$), 24.5 (CH), 38.0 (CH$_2$), 59.0 and 59.1 (CH$_2$), 63.8 and 64.5 (CH$_2$), 64.8 and 64.8 (CH$_2$), 67.4 and 67.6 (CH$_2$), 69.0 and 69.1 (CH$_2$), 72.6 and 73.3 (CH), 114.7 and 115.0 (CH), 170.1 (C$_{quart}$).

ESI-HR: calculated [C$_{13}$H$_{24}$NaO$_6$$^+$]=299.1465, measured: [C$_{13}$H$_{24}$NaO$_6$$^+$]=299.1466

Elemental analysis: calculated for C$_{13}$H$_{24}$NaO$_6$ (276.3 g/mol): C=56.51%, H=8.75%, measured: C=56.36%, H=8.47%.

2-[3-(3-methylbutoxy)-2-oxopropyl]-1,3-dioxolan-4-yl acetate

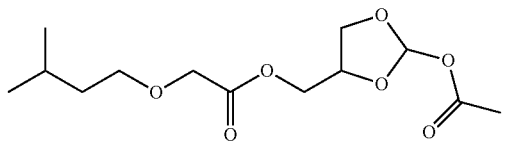 [SMILES: CC(=O)OC1OCC(COC(=O)COCCC(C)C)O1]

5 g (18.09 mmol) of 1-(4-ethoxy-1,3-dioxolan-2-yl)-3-(3-methylbutoxy)propan-2-one were heated together with 1.85 g of acetic anhydride and 832 mg of formic acid for four hours in the microwave reactor at 60° C.

$^1$H-NMR (600 MHz, CDCl$_3$): d=0.91 (d, J=6.7 Hz, 6H), 1.48-1.56 (q, J=6.8 Hz, 2H), 1.62-1.79 (m, 1H), 2.22 (s, 3H), 3.63 (t, J=7.1 Hz, 2H), 4.11 (s, 2H), 4.13-4.57 (m, 5H), 6.88 and 6.89 (s and s, 1H).

Release of Allyl Isoamyl Glycolate

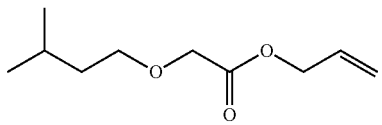

The 2-[3-(3-methylbutoxy)-2-oxopropyl]-1,3-dioxolan-4-yl acetate was not isolated but rather was dissolved in CDCl$_3$, with 1,4-dibromobenzene being added as internal standard. Heating to 150° C. then took place in the microwave.

The olefinic signals of allyl isoamyl glycolate appeared after 8 min.

While at least one exemplary embodiment has been presented in the foregoing detailed description, it should be appreciated that a vast number of variations exist. It should also be appreciated that the exemplary embodiment or exemplary embodiments are only examples, and are not intended to limit the scope, applicability, or configuration of the various embodiments in any way. Rather, the foregoing detailed description will provide those skilled in the art with a convenient road map for implementing an exemplary embodiment as contemplated herein. It being understood that various changes may be made in the function and arrangement of elements described in an exemplary embodiment without departing from the scope of the various embodiments as set forth in the appended claims.

The invention claimed is:

1. A compound of formula (I)

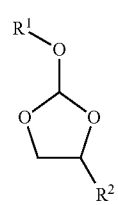

Formula (I)

wherein

R$^1$ and R$^2$ are each independently of one another selected from the group of:
- a linear, aliphatic, olefinic or open-chain organic residue having 2 to 20 carbon atoms and 0 to 10 heteroatoms selected from N, O, S and Si;
- a branched or cyclic organic residue having 3 to 20 carbon atoms and 0 to 10 heteroatoms selected from N, O, S and Si; and
- an aromatic or heteroaromatic organic residue having 4 to 20 carbon atoms and 0 to 10 heteroatoms selected from N, O, S and Si, wherein R$^2$ is a residue derived from a fragrance alkene.

2. The compound according to claim 1, wherein R$^1$ and R$^2$ are independently selected from the group of:

substituted or unsubstituted, linear or branched alkyl, alkenyl or alkynyl having up to 20 carbon atoms;
substituted or unsubstituted, linear or branched heteroalkyl, heteroalkenyl or heteroalkynyl having up to 20 carbon atoms, and 1 to 6 heteroatoms selected from O, S and N;
substituted or unsubstituted aryl having up to 20 carbon atoms;
substituted or unsubstituted heteroaryl having up to 20 carbon atoms, and 1 to 6 heteroatoms selected from O, S and N;
cycloalkyl or cycloalkenyl having up to 20 carbon atoms; and
heterocycloalkyl or heterocycloalkenyl having up to 20 carbon atoms, and 1 to 6 heteroatoms selected from O, S and N.

3. The compound according to claim 1, wherein $R^1$ is
a. a residue of formula —C(O)—$R^3$, —CH$_2$—C(O)—$R^3$, -aryl, -heteroaryl, —CH$_2$-aryl or —CH$_2$-heteroaryl, wherein $R^3$ is selected from the group of:
   hydrogen, substituted or unsubstituted, linear or branched alkyl, alkenyl or alkynyl having up to 20 carbon atoms,
   substituted or unsubstituted, linear or branched heteroalkyl, heteroalkenyl or heteroalkynyl having up to 20 carbon atoms, and 1 to 6 heteroatoms selected from O, S and N,
   substituted or unsubstituted aryl having up to 20 carbon atoms,
   substituted or unsubstituted heteroaryl having up to 20 carbon atoms, and 1 to 6 heteroatoms selected from O, S and N, and
   cycloalkyl or cycloalkenyl having up to 20 carbon atoms, and heterocycloalkyl or heterocycloalkenyl having up to 20 carbon atoms, and 1 to 6 heteroatoms selected from O, S and N;
b. a residue of formula —C(O)—$R^3$, wherein $R^3$ is a substituted or unsubstituted, linear or branched alkyl having up to 5 carbon atoms; or
c. a substituted or unsubstituted, linear or branched alkyl having 1 to 5 carbon atoms.

4. The compound according to claim 1, wherein $R^2$
a. is an organic residue having 4 to 10 carbon atoms; and/or
b. comprises at least one heteroatoms selected from N, O, S, Si, F, Cl and Br; and/or
c. comprises at least one cyclic group; and/or
d. comprises at least one carbonyl group (—C(=O)—; and/or is a residue of formula $C_{1-10}$-alkyl-O—(CH$_2$)$_p$—C(O)O—(CH$_2$)$_q$—, wherein p and q independently are 0 or an integer from 1 to 6.

5. The compound according to claim 1, wherein $R^1$ is a fragrance alcohol, and wherein the fragrance alkene of $R^2$ and the fragrance alcohol of $R^1$ are selected from the group consisting of acetovanillone, allyl amyl glycolate, allyl isoamyl glycolate, alpha-amyl cinnamyl alcohol, anisyl alcohol, benzoin, benzyl alcohol, benzyl salicylate, 1-butanol, butyl lactate, 2-t-butyl-5-methylphenol, 2-t-butyl-6-methylphenol, carvacrol, carveol, 4-carvomenthenol, cedrol, cetyl alcohol, cinnamic alcohol, citronellol, o-cresol, m-cresol, p-cresol, crotyl alcohol, decahydro-2-naphthol, 1-decanol, 1-decen-3-ol, 9-decen-1-ol, diethyl malate, diethyl tartrate, dihydrocarveol, dihydromyrcenol, 2,6-diisopropylphenol, dimethicone copolyol, 2,6-dimethoxyphenol, 1,1-dimethoxy-3,7-dimethyloctan-7-ol, 2,6-dimethyl-4-heptanol, 2,6-dimethylheptan-2-ol, 6,8-dimethyl-2-nonanol, 3,7-dimethyl-2,6-octadien-1-ol, 3,7-dimethyl-1,6-octadien-3-ol, 3,7-dimethyl-1-octanol, 3,7-dimethyl-3-octanol, 3,7-dimethyl-6-octen-1-ol, 3,7-dimethyl-7-octen-1-ol, dimetol, 2-ethylfenchol, 4-ethylguaiacol, 2-ethyl-1-hexanol, ethyl 2-hydroxybenzoate, ethyl 3-hydroxybutyrate, 3-ethyl-2-hydroxy-2-cyclopenten-1-one, ethyl 2-hydroxycaproate, ethyl 3-hydroxyhexanoate, ethyl lactate, ethyl maltol, p-ethylphenol, ethyl salicylate, eugenol, farnesol, fenchyl alcohol, geraniol, glucose pentaacetate, glycerol, glyceryl monostearate, guaiacol, 1-heptanol, 2-heptanol, 3-heptanol, cis-4-heptenol, cis-3-heptenol, n-hexanol, 2-hexanol, 3-hexanol, cis-2-hexenol, cis-3-hexenol, trans-3-hexenol, 4-hexenol, cis-3-hexenyl hydrocinnamyl alcohol, 2-hydroxybenzoate, 2-hydroxyacetophenone, 4-hydroxybenzyl alcohol, 3-hydroxy-2-butanone, hydroxycitronellal, 4-(4-hydroxy-3-methoxyphenyl)-2-butanone, 2-hydroxy-3-methyl-2-cyclopenten-1-one, 4-(p-hydroxyphenyl)-2-butanone, 2-hydroxy-3,5,5-trimethyl-2-cyclohexenone, delta-isoascorbic acid, isoborneol, isoeugenol, isophytol, isopropyl alcohol, p-isopropyl benzyl alcohol, 4-isopropylcyclohexanol, 3-isopropylphenol, 4-isopropylphenol, 2-isopropylphenol, isopulegol, lauryl alcohol, linalool, maltol, menthol, 4-methoxybenzyl alcohol, 2-methoxy-4-methylphenol, 2-methoxy-4-propylphenol, 2-methoxy-4-vinylphenol, α-methylbenzyl alcohol, 2-methylbutanol, 3-methyl-2-butanol, 3-methyl-2-buten-1-ol, 2-methyl-3-buten-2-ol, methyl 2,4-dihydroxy-3,6-dimethylbenzoate, 4-methyl-2,6-dimethoxyphenol, methyl N-3,7-dimethyl-7-hydroxyoctylideneanthranilate, methyl 3-hydroxyhexanoate, 6-methyl-5-hepten-2-ol, 2-methylpentanol, 3-methyl-3-pentanol, 2-methyl-4-phenylbutan-2-ol, 2-methyl-3-phenylpropan-2-ol, methyl salicylate, 3-methyl-5-(2,2,3-trimethyl-3-cyclopenten-1-yl)-4-penten-2-ol, 2-methyl-2-vinyl-5-(1-hydroxy-1-methylethyl)-3,4-dihydrofuran, myrtenol, neohesperidin dihydrochalcone, neomenthol, nerol, nerolidol, trans-2-cis-6-nonadienol, 1,3-nonanediol acetate, nonadyl, 2-nonanol, cis-6-nonen-1-ol, trans-2-nonen-1-ol, nonyl alcohol, 1-octanol, 2-octanol, 3-octanol, cis-3-octen-1-ol, cis-2-octen-1-ol, trans-2-octen-1-ol, cis-6-octen-1-ol, cis-octen-1-ol, 1-octen-3-ol, oleyl alcohol, patchouli alcohol, 3-pentanol, n-pentanol, 2-pentanol, 1-penten-1-ol, cis-2-penten-1-ol, perillyl alcohol, 2-phenoxyethanol arabinogalactan, beta-phenethyl alcohol, phenethyl salicylate, phenol, phenylacetaldehyde glyceryl acetal, 3-phenyl-1-pentanol, 5-phenyl-1-pentanol, 1-phenyl-1-pentanol, 1-phenyl-2-pentanol, 1-phenyl-3-methyl-1-pentanol, phytol, pinacol, polyalkylene glycol, Polysorbate 20, , Polysorbate 60, Polysorbate 80, , prenol, n-propanol, propenyl guaethol, propylene glycol, 2-propylphenol, 4-propylphenol, resorcinol, retinol, salicylaldehyde, sorbitan monostearate, sorbitol, stearyl alcohol, syringaldehyde, α-terpineol, tetrahydrogeraniol, tetrahydrolinalool, tetrahydromyrcenol, thymol, triethyl citrate, 1,2,6-trihydroxyhexane, p-alpha, alpha-trimethylbenzyl alcohol, 2-(5, 5,6-trimethylbicyclo[2.2.1]hept-2-yl)cyclohexanol, 5-(2,2,3-trimethyl-3-cyclopentenyl)-3-methylpentan-2-ol, 3,7,11-trimethyl-2,6,10-dodecatrien-1-ol, 3,7,11-trimethyl-1,6,10-dodecatrien-3-ol, 3,5,5-trimethyl-1-hexanol, 10-undecen-1-ol, undecyl alcohol, vanillin, o-vanillin, vanillyl butyl ether, 4-vinylphenol, 2,5-xylenol, 2,6-xylenol, 3,5-xylenol, 2,4-xylenol, xylose, 5-(2-methylpropyl)-1-methyl-1-cyclohexene, 1-methylidene-3-(2-methylpropyl)cyclohexane, and myrcene.

6. The compound according to claim 1, wherein the compound is a compound of formula (II)

Formula (II)

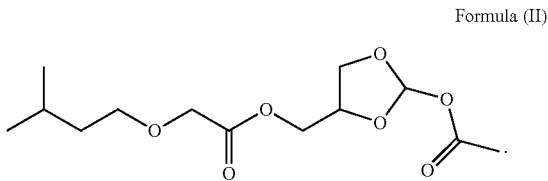 [SMILES: CC(=O)OC1OCC(COC(=O)COCCC(C)C)O1]

7. A detergent or cleaning agent comprising at least one compound of formula (I)

Formula (I)

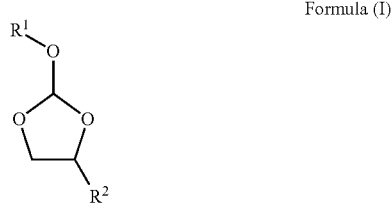

wherein
R$^1$ and R$^2$ are each independently of one another selected from the group of:
a linear, aliphatic, olefinic or open-chain organic residue having 2 to 20 carbon atoms and 0 to 10 heteroatoms selected from N, O, S and Si;
a branched or cyclic organic residue having 3 to 20 carbon atoms and 0 to 10 heteroatoms selected from N, O, S and Si; and
an aromatic or heteroaromatic organic residue having 4 to 20 carbon atoms and 0 to 10 heteroatoms selected from N, O, S and Si.

8. The detergent or cleaning agent according to claim 7, wherein
a. the at least one compound is comprised in amounts between about 0.0001 and about 5% by weight, based on the total agent, and/or
b. the agent comprises at least one surfactant selected from the group of anionic, cationic, nonionic, zwitterionic, amphoteric surfactants and mixtures thereof, and/or
c. it is in liquid or solid form.

9. A method for fragrancing surfaces, the method comprising:
applying a compound of formula (I) to the surface to be fragranced, wherein formula (I) is as follows:

Formula (I)

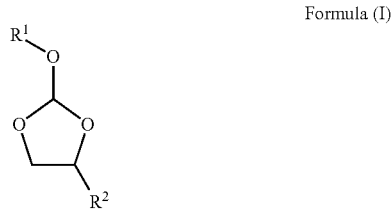

wherein
R$^1$ and R$^2$ are each independently of one another selected from the group of:
a linear, aliphatic, olefinic or open-chain organic residue having 2 to 20 carbon atoms and 0 to 10 heteroatoms selected from N, O, S and Si;
a branched or cyclic organic residue having 3 to 20 carbon atoms and 0 to 10 heteroatoms selected from N, O, S and Si; and
an aromatic or heteroaromatic organic residue having 4 to 20 carbon atoms and 0 to 10 heteroatoms selected from N, O, S and Si;
heating the compound to a temperature of from about 20° C. to about 250° C.; and/or
contacting the compound with a Lewis acid and/or Brønsted acid.

10. The compound according to claim 1, wherein R$^1$ and R$^2$ are each independently of one another the linear, aliphatic, olefinic or open-chain organic residue having 2 to 20 carbon atoms and 0 to 10 heteroatoms selected from N, O, S and Si.

11. The compound according to claim 1, wherein R$^1$ and R$^2$ are each independently of one another the branched or cyclic organic residue having 3 to 20 carbon atoms and 0 to 10 heteroatoms selected from N, O, S and Si.

12. The compound according to claim 1, wherein R$^1$ and R$^2$ are each independently of one another the aromatic or heteroaromatic organic residue having 4 to 20 carbon atoms and 0 to 10 heteroatoms selected from N, O, S and Si.

13. The compound according to claim 2, wherein R$^1$ and R$^2$ are independently of one another the substituted or unsubstituted, linear or branched alkyl, alkenyl or alkynyl having up to 20 carbon atoms.

14. The compound according to claim 2, wherein R$^1$ and R$^2$ are independently of one another the substituted or unsubstituted, linear or branched heteroalkyl, heteroalkenyl or heteroalkynyl having up to 20 carbon atoms, and 1 to 6 heteroatoms selected from O, S and N.

15. The compound according to claim 2, wherein R$^1$ and R$^2$ are independently of one another the substituted or unsubstituted aryl having up to 20 carbon atoms.

16. The compound according to claim 2, wherein R$^1$ and R$^2$ are independently of one another the substituted or unsubstituted heteroaryl having up to 20 carbon atoms, and 1 to 6 heteroatoms selected from O, S and N.

17. The compound according to claim 2, wherein R$^1$ and R$^2$ are independently of one another the cycloalkyl or cycloalkenyl having up to 20 carbon atoms.

18. The compound according to claim 2, wherein R$^1$ and R$^2$ are independently of one another the heterocycloalkyl or heterocycloalkenyl having up to 20 carbon atoms, and 1 to 6 heteroatoms selected from O, S and N.

* * * * *